(12) United States Patent
Thurston et al.

(10) Patent No.: US 6,503,481 B1
(45) Date of Patent: Jan. 7, 2003

(54) COMPOSITIONS FOR AEROSOLIZATION AND INHALATION

(75) Inventors: Rachel M. Thurston, Columbus, OH (US); James D. Browning, Columbus, OH (US); Praful K. Shah, Cincinnati, OH (US); Michael E. Placke, Columbus, OH (US)

(73) Assignee: BattellePharma, Inc., Columbus, OH (US)

( * ) Notice: Subject to any disclaimer, the term of this patent is extended or adjusted under 35 U.S.C. 154(b) by 0 days.

(21) Appl. No.: 09/561,648

(22) Filed: May 2, 2000

Related U.S. Application Data

(60) Provisional application No. 60/132,215, filed on May 3, 1999.

(51) Int. Cl.[7] .................. A61M 11/00; A61M 15/00; A61K 9/12; A61K 9/72; B05B 5/00
(52) U.S. Cl. ............... 424/45; 424/43; 424/44; 424/1.13; 424/1.61; 424/1.65; 514/2; 514/12; 128/200.14; 128/200.21; 239/690; 239/708; 239/704
(58) Field of Search ............................. 239/690, 708, 239/704; 514/2, 12; 424/1.13, 1.61, 1.65, 43, 44, 45; 128/200.14, 200.21

(56) References Cited

U.S. PATENT DOCUMENTS

| | | | |
|---|---|---|---|
| 4,659,012 A | | 4/1987 | Coffee |
| 4,829,996 A | | 5/1989 | Noakes et al. |
| 5,578,567 A | * | 11/1996 | Cardinaux et al. ............ 514/12 |
| 5,660,166 A | | 8/1997 | Lloyd et al. |
| 5,813,614 A | * | 9/1998 | Coffee ........................ 239/690 |
| 6,105,571 A | | 8/2000 | Coffee |
| 6,158,431 A | | 12/2000 | Poole |

FOREIGN PATENT DOCUMENTS

| | | |
|---|---|---|
| EP | 0 234 842 A2 | 9/1987 |
| WO | WO94/14543 A2 | 7/1994 |
| WO | WO95/26235 A1 | 10/1995 |
| WO | WO99/07478 A1 | 2/1999 |
| WO | WO99/42153 A1 | 8/1999 |
| WO | WO99/49981 A1 | 10/1999 |
| WO | WO00/35524 A2 | 6/2000 |
| WO | WO00/38770 A2 | 7/2000 |

* cited by examiner

*Primary Examiner*—Frederick Krass
*Assistant Examiner*—Clinton Ostrup
(74) *Attorney, Agent, or Firm*—Patricia A. Coburn

(57) ABSTRACT

A composition used in combination with an electrohydrodynamic device capable of delivering an active ingredient to the aerodigestive system of the user. The composition comprises three or optionally four basic components: an active ingredient; a carrier material in which the active ingredient may be dissolved, suspended, or emulsified; an aerosol properties adjusting material which provides the composition with the physical characteristics required to create an aerosol cloud by electrostatic or electrohydrodynamic means; and optionally at least one excipient that further adjusts, preserves, stabilizes, or enhances the overall performance of the composition.

18 Claims, No Drawings

COMPOSITIONS FOR AEROSOLIZATION AND INHALATION

This patent application claims the benefit of U.S. Provisional Patent Application No. 60/132,215, filed May 3, 1999, entitled "Therapeutic Formulations for Aerosolization and Inhalation," the disclosure of which is incorporated as if fully rewritten herein.

BACKGROUND OF THE INVENTION

This invention relates to compositions for aerosolization and delivery to the user's aerodigestive system by inhalation of the aerosolized composition, as well methods for making and using these compositions.

Administration of active ingredients directly to the aerodigestive system (i.e., the pulmonary system and/or digestive tract) of a patient by means of an inhaled aerosol may be preferable to other methods of drug delivery in certain circumstances. Delivery of drugs or other active ingredients directly to the patient's lungs provides numerous advantages including: providing an extensive surface area for drug absorption, direct delivery of therapeutic agents to the disease site in the case of regional drug therapy, eliminating the possibility of drug degradation in the patient's intestinal tract (a risk associated with oral administration), and eliminating the need for repeated subcutaneous injections. Furthermore, delivery of drugs to the pulmonary system by means of aerosol inhalation may be used to deliver drugs systemically, as well as for targeted local drug delivery for treatment of respiratory ailments such as lung cancer or asthma.

At the present time, inhalation therapy is a rapidly evolving technology. Numerous active ingredients are being developed with the expectation that effective delivery of and treatment with these agents will be possible by means of inhaled aerosols. Aerosolizing active ingredients requires a composition with certain characteristics and properties that make the composition compatible with the aerosolization process. The process of formulating particular active ingredients, such as drugs, with the appropriate carriers, such as organic solvents, can be particularly challenging. Therefore, there is a need for basic or general compositions which are compatible with a variety of active ingredients, a range of suitable carriers, and appropriate aerosol generating devices.

Important considerations in administering an aerosolized active ingredient to the lungs of a patient include the characteristics of both the composition containing the active ingredient, and the aerosol cloud that will ultimately be inhaled by the patient or user. The composition must be a suitable carrier for the active ingredient, the active ingredient must be stable for a period of time in the composition, the composition must be consistently sprayable through an aerosol-generating device, and the composition must be well-tolerated by the user. Furthermore, the aerosol-generating device itself must effectively and consistently convert the formula into an aerosol cloud with certain desired properties. For example, an aerosol-generating device should not deliver a high velocity aerosol which makes it difficult for the user to inhale aerosol particles. Preferred aerosol characteristics also include an aerosol cloud composed of particles that are roughly uniform in size. An aerosol cloud composed of uniform particles of a predetermined size provides the most efficient and effective delivery of the therapeutic composition to the patient or user because the dosage that the patient receives can be more precisely controlled (i.e., uniform particle size equals more precise delivery and dosage). Therefore, for maximum effectiveness of both drug and aerosol device, consistent generation of uniformly sized aerosol particles most occur each time the composition is aerosolized with a particular device.

Aerosol devices currently used in the clinical context include metered dose inhalers, dry powder inhalers, and nebulizers. Although effective at creating aerosols, these devices typically do not permit the device user to control either the particle size of the aerosol cloud to be inhaled, or the velocity of the aerosol delivered by the device. The particle size distribution of aerosols generated with these devices is usually too broad or too varied to effectively and consistently deliver the composition to the deep lungs of the user. As a consequence, pulmonary administration of a active ingredient may be less than optimal when using metered dose inhalers, dry powder inhalers, or nebulizers due to deposition of the composition in the mouth or throat of the user or due to exhalation of the composition by the user.

U.S. Pat. No. 4,829,996 to Noakes et al., and U.S. Pat. No. 5,707,352 to Sekins et al. both disclose formulations suitable for use with aerosol devices; however, these devices and formulas are suboptimal when compared with the performance of electohydrodynamic (EHD) aerosol systems. EHD aerosol generators are capable of generating aerosols in which particle size, aerosol velocity, and the resultant deposition patterns can be more precisely controlled. EHD aerosol generators, therefore, are ideal devices for use with therapeutic compositions that are to be delivered to the patient's pulmonary system by inhalation. Thus, there is a need for therapeutic compositions that are compatible with both a variety of active ingredients as well as electrostatic and EHD aerosol generating devices.

SUMMARY OF THE INVENTION

The present invention includes general compositions capable of: being aerosolized; inhaled by the user; delivering a predetermined dosage of a active ingredient to the lungs of the user; and which are optimized for use with an electrohydrodynamic aerosol generator. These compositions may contain two or more basic components which may be present in a variety of combinations, concentrations, and ratios to one another.

In a preferred embodiment of the present invention, the general composition comprises four basic, or fundamental, components. The first component is a active ingredient; examples of which include drugs, vaccines, and proteins. The second component of the therapeutic composition is a carrier material in which the active ingredient may be dissolved, suspended, or emulsified; examples of which include water or alcohol. The third component of the therapeutic composition is an aerosol properties adjusting material, which adjusts the physical properties of the liquid composition to be within ranges desired for aerosolization with an electrostatic or electrohydrodynamic device. In some embodiments of the invention the carrier material may act as the property adjusting material so as to bring the composition within the desired ranges of physical or chemical properties. In such cases no additional third basic component is required. The fourth optional component of the basic composition is at least one excipient that individually or in combination with other excipients preserves, stabilizes, or enhances the overall performance of the therapeutic composition. Examples of suitable excipients include ionic materials, surfactants, and antimicrobial agents.

Therefore, it is an object of the present invention is to provide a general base composition that includes a suitable carrier for a variety of active ingredients, and in which the active ingredients will be stable for an extended period of time.

Another object of the present invention is to provide a base composition which is compatible with electrostatic or electrohydrodynamic aerosol generating devices.

A further object of the present invention is to provide a liquid composition with a commercially reasonable shelf-life.

Further objects, advantages, and novel aspects of this invention will become apparent from a consideration of the subsequent detailed description.

DETAILED DESCRIPTION OF THE INVENTION

Broadly, the present invention provides compositions, and methods for making and using compositions, which have certain preferred characteristics and properties required for generating aerosols also having particular preferred characteristics. In a preferred embodiment of the present invention, the compositions are aerosolized with an electrostatic or electrohydrodynamic (EHD) aerosol generating device. A typical embodiment of this invention includes a liquid composition having predetermined physical and chemical properties which facilitate aerosolization of the composition with an EHD aerosol device. This liquid composition typically includes three or four basic components which are (i) an active ingredient; (ii) a liquid carrier for the active ingredient; (iii) an aerosol properties adjusting material; and optionally (iv) at least one excipient. The combination of these components provides a therapeutic composition having enhanced properties for delivery to a user by means of generating an inhalable aerosol.

Electrohydrodynamic Aerosols

The therapeutic compositions of this invention must be compatible with an aerosol-generating device so that an aerosol cloud with certain preferred properties and characteristics is reproduced each time the device is used. Aerosols having uniformly-sized particles and uniform distribution patterns are desirable over aerosols that do not possess these characteristics because they exhibit more desirable deposition properties within the aerodigestive tract of the user (i.e., they have a higher respirable fraction). When used with compatible compositions, EHD aerosol generating devices can be adjusted to create substantially monomodal aerosols having particles more uniform in size than aerosols generated by other devices or methods.

Typical EHD devices include a spray nozzle in fluid communication with a source of liquid to be aerosolized, at least one discharge electrode, a first voltage source for maintaining the spray nozzle at a negative (or positive) potential relative to the potential of the discharge electrode, and a second voltage source for maintaining the discharge electrode at a positive (or negative) potential relative to the potential of the spray nozzle. Most EHD devices create aerosols by causing a liquid to form droplets that enter a region of high electric field strength. The electric field then imparts a net electric charge to these droplets, and this net electric charge tends to remain on the surface of the droplet. The repelling force of the charge on the surface of the droplet balances against the surface tension of the liquid in the droplet, thereby causing the droplet to form a cone-like structure known as a Taylor Cone. In the tip of this cone-like structure, the electric force exerted on the surface of the droplet overcomes the surface tension of the liquid, thereby generating a stream of liquid that disperses into a many smaller droplets of roughly the same size. These smaller droplets form a mist which constitutes the aerosol cloud that the user ultimately inhales.

Physical Characteristics of Liquid Composition

Liquid compositions that are compatible with EHD aerosol generating devices must have characteristics and properties that fall within certain parameters for the aerosol cloud to have the desired properties. In a preferred embodiment of the present invention, the most relevant physical characteristics of the composition include surface tension, electrical resistivity, and electrical permittivity (dielectric constant). Additionally, viscosity of the composition can also be of importance in preparing liquid therapeutic compositions for use with electrostatic or EHD devices.

Surface tension is a property possessed by liquid surfaces whereby these surfaces behave as if covered by a thin elastic membrane in a state of tension. Surface tension is a measure of the energy needed to increase the surface area of the liquid; therefore, liquids with a lower surface tension will aerosolize more easily than liquids with higher surface tension. Surface tension is measured by the force acting normally across unit length in the surface. The phenomenon of surface tension is due to unbalanced molecular cohesive forces near the surface of a liquid. In a broad embodiment of the present invention, the surface tension of the composition is typically within the range of about 10 to 72 milliNewtons/meter. In another embodiment of the present invention, the surface tension of the composition is typically within the range of about 15 to 45 milliNewtons/meter. In a preferred embodiment of the present invention, the surface tension of the composition is typically within the range of about 20 to 35 milliNewtons/meter.

Electrical conductivity is the ability of a solution to transport electrical charge. The inverse of electrical conductivity is electrical resistivity. Thus, electrical resistivity is a measure of the ability of a material to resist the transport of electrical current, and is a property of a conductor, which gives the resistance in terms of the conductor's dimensions. Liquid compositions with resistivity values of 10 to 100,000 ohm-meters can be aerosolized using EHD aerosol devices, provided that other relevant physical properties are within optimal operating parameters. Thus, in a broad embodiment of the present invention, the electrical resistivity of the composition is typically within the range of about 10 to 100,000 ohm-meters. In another embodiment of the present invention, the electrical resistivity of the composition is typically within the range of about 50 to 10,000 ohm-meters. In a preferred embodiment of the present invention, the electrical resistivity of the liquid composition is typically within the is range of about 200 to 2000 ohm-meters.

Electrical permittivity is a measure of the polarizibility of a liquid, and is relevant in electrostatic spraying processes as it describes the increase in electrical field strength where a fluid is present. To aerosolize solvents with high permittivity (e.g., water), a higher electrical field strength (voltage) is required. The permittivity of a liquid composition is not significantly affected by the addition of a small amount (less than 5%) of non-ionic excipients or solvents. In a broad embodiment of the present invention, the electrical permittivity of the composition is typically within the range of about 5 to 500. In another embodiment of the present invention, the electrical permittivity is typically within the range of about 10 to 150. In a preferred embodiment of the present invention, the electrical permittivity of the composition is typically within the range of about 15 to 50.

Electrical permittivity is a dimensionless value denoting the ration of the electrical permittivity of a liquid or material to that of a vacuum.

Viscosity is the measure of the resistance to fluid flow; thus solutions that flow easily generally have lower viscosity. The viscosity of a liquid composition is not affected significantly by the addition of small amounts of drug to the composition. However, the addition of certain suspending agents or very high concentrations of drugs can increase the viscosity of the liquid composition. Viscosity may not be a key solvent parameter in aerosolization of the present invention, but it does affect particle size distribution. Highly viscous materials tend to form aerosols with more disperse or bimodal distributions, and with particle sizes larger than desired for respirable aerosols.

Liquid compositions having physical properties within the optimal parameters disclosed above will aerosolize when used with most EHD devices. In the present invention, controlling the voltage delivered to the system to create the region of high electric field strength also controls the particle size of the aerosol cloud generated by an EHD device. In a broad embodiment of the present invention directed toward inhalation, the size of respirable aerosol particles is typically about 0.1 to 10.0 micrometers. Aerosol particles at the lower end of this range are required for delivery of the liquid composition to the deep lung, while aerosol particles at the upper end of this range are required for delivery of the composition to the proximal respiratory tract. For deposition of the composition in the central and peripheral areas of the lung, the preferred size of the aerosol particles is about 1.0 to 6.0 micrometers.

Active Ingredient

To benefit the user, the aerosolized liquid composition of the present invention contains at least one active ingredient at a concentration permitting delivery of the desired dosage to the patient. The number and types of active ingredients suitable for delivery to a patient by means of an inhaled aerosol varies widely and includes numerous options. A preferred embodiment of the present invention typically includes at least one active ingredient which may be any of the following: small molecule and synthetic drugs such as sodium cromoglycate, albuterol sulfate, and triamcinolone acetonide; chemo-therapeutic or chemopreventive agents such as paclitaxel and doxorubicin; vaccines; nucleic acids, including DNA and RNA vectors and vaccines; aptamers, proteins such as insulin; gene therapy agents for treating diseases such as cystic fibrosis; enzymes, hormones; antibodies; vitamins; peptides and polypeptides; oligonucleotides; cells; antigens; allergens; pulmonary surfactant and other surfactants (including synthetic surfactants); anti-infectious agents including antimicrobials, antibiotics, antifungals and antivirals; and pain management drugs such as narcotics.

Preferred initial concentrations of active ingredients in the composition are determined by the required effective dosage of each active ingredient, as well as the efficiency of the pulmonary delivery of the inhaled aerosol. Delivery efficiency and drug efficacy is typically impacted by the selected deposition site within the user's lung.

Carrier Material

In the present invention, the composition to be aerosolized also provides a carrier in which the active ingredient may be dissolved, suspended or emulsified. A variety of solvents or emulsifying agents are suitable for this purpose. In a typical embodiment of the present invention, either water or ethanol (depending on the solubility characteristics of the active ingredient) is used as the solvent in which the active ingredient may be dissolved or suspended. In a preferred embodiment, the carrier (solvent) fraction of the composition may represent 5 to 95% of the total volume of the composition. In other embodiments, the fraction of the composition represented by the carrier varies depending on the solubility or insolubility of the active ingredient. For example, if a active ingredient is highly soluble in the carrier (e.g. water), then the carrier fraction of the total composition may be as low as about 5% to 10%. If an active ingredient is only moderately soluble in water, a larger fraction of water may be required to completely dissolve or sufficiently suspend the active ingredient.

The pH of desired solvent, as well as the pH of the entire composition, may impact the solubility and stability of the active ingredient. Although pH requirements are likely to differ among specific compositions depending on the active ingredient being used, pH ranges useful in the present invention for the liquid carrier may be in the range of pH about 2 to 9. Preferably, a pH range of about 3 to 8 is used, and most preferably a pH range of about 5 to 8 is used.

In a preferred embodiment of the present invention, the solvents selected as carriers are chosen for use as carriers based both on compatibility with certain active ingredients and on their compatibility with EHD devices, and typically include water or ethanol. In an alternative embodiment, phospholipids or pulmonary surfactant is used as a carrier. In still another embodiment, other alcohols such as isopropanol are employed as carriers. In other embodiments of the present invention, perfluoronated compounds such as perfluorooctanol and perfluorodecalin are substituted for some or all of the water or ethanol as the carrier material. Such perfluoronated compounds are useful as alternative carriers for drugs soluble in perfluoronated carriers, microsuspended medicaments or emulsified mixtures of such pharmaceutical products in water.

Aerosol Properties Adjusting Material

Certain physical properties of a liquid composition are critical in enhancing the effectiveness of aerosolization of the composition with an electrostactic or EHD device. Therefore, in the present invention, an aerosol properties adjusting material that provides the desired physical characteristics to the composition represents another possible fraction of the total volume of the liquid composition. In a broad embodiment of this invention, the physical properties of the liquid composition typically comprise: (i) a surface tension of about 10 to 72 milliNewtons/meter; (ii) an electrical resistivity of about 5 to 100,000 ohm-meters; and (iii) and an electrical permittivity of about 5 to 500. In some embodiments, it may be possible to achieve a liquid composition with physical properties falling within these parameters by simply combining the active ingredient and the carrier material. However, if the combination of the active ingredient and the carrier material does not produce a liquid composition having physical properties falling within these parameters, the addition of the aerosol properties adjusting material will bring the composition within the required parameters.

In a preferred embodiment of the invention, the aerosol properties adjusting material is present as about a 5 to 90% fraction of the total volume of the composition. The volume of the aerosol properties adjusting material fraction will vary depending on the volume of the carrier that is required. For example, if the carrier represents 20% of the total volume of the composition, the aerosol properties adjusting material could represent the remaining 80% of the total volume. The 20/80 volume ratio can apply even with the active ingredient present because the active ingredient is dissolved in the carrier and/or aerosol property adjusting material. In some instances, the carrier itself may serve as the aerosol properties adjusting material.

In a preferred embodiment of the present invention, the aerosol properties adjusting material may be at least one of the following materials or their derivatives; ethanol or other alcohols; propylene glycol; polyethylene glycol; glycerol; oleic acid; medium chain triglycerides; fatty acids; soybean oil; olive oil; phospholipids, and perfluorocarbons. Combinations of these materials is advantageous in some embodiments. For example, the use of ethanol alone may create an aerosol, but the particle size of the aerosol may be below the preferred range. By combining ethanol and polyethylene glycol in a predetermined ratio to one another, the preferred particle size can be achieved. In one embodiment of the present invention, the aerosol enhancing component comprises 80% ethanol and 10% polyethylene glycol for a fraction representing 90% of the total volume of the liquid composition.

Excipient

As discussed, there are acceptable ranges of solvent parameters that permit a liquid composition to be aerosolized by the electrohydrodynamic process. Due to the characteristics of certain active ingredients (e.g., ionic, solubility limits, etc.) it may be difficult to formulate a drug at desired concentrations in an appropriate carrier solvent while remaining within the required solvent parameter values. The addition of an excipient can alter a solvent parameter and bring the composition back within the optimal ranges. Addition of an excipient is necessary only in embodiments of the present invention in which the combined active ingredient, carrier material, and aerosol properties adjusting material do not yield an aerosol with all of the desired characteristics.

Various embodiment of the present invention include at least one excipient or a combination of excipients. A broad definition of an excipient is anything in a composition other than an active ingredient. In the more narrow context of the present invention, an excipient is added for a variety of purposes including: stabilization of the liquid composition; facilitating control of aerosol particle size; increasing the solubility of the active ingredient in the composition; and lowering the surface tension of the liquid.

Once solubilized, suspended or emulsified, the active ingredient must also be stable in the carrier itself, and stable in the final composition. Stability requires that the active ingredient not lose activity prior to aerosolization (i.e. retains a reasonable shelf-life), and that the active ingredient not lose activity or degrade significantly as a result of the process of aerosolization. Furthermore, the complete composition must itself be stable over time. In various embodiments, stability issues can be addressed by the addition of a stabilizing excipient to the composition.

In a preferred embodiment of the present invention, at least one of the following excipients is added to increase physical stability of the composition: oils, glycerides, polysorbates, celluloses lecithin, polyvinyl pyrrolidone, polyethyl glycol, saccharide gums, and alginates; while ascorbic acid, citric acid, cyclodextrin, tocopherols or other antioxidants are added to increase chemical stability. In another embodiment of the present invention, chelating or complexing agents such as citric acid, cyclodextrins, and ethylenediaminetetracetic acid may be added to stabilize drug compositions and to increase the solubility of the active ingredient in the composition.

In other embodiments, antioxidants such as ascorbic acid and ascorbic acid esters, Vitamin E, tocopherols, butylated hydroxyanisole, and butylated hydroxytoluene are added to reduce degradation of a drug composition caused by oxidation.

An excipient may also be added as a preservative to maintain the microbial integrity of the therapeutic composition. In one embodiment of the present invention, at least one of the following excipients is added to preserve compositions against microbial contamination or attack: benzalkonium chlorides, phenol, parabens, or any other acceptable antimicrobial or antifungal agent.

By further adjusting physical properties, the addition of excipients may also enhance the overall performance of the composition in terms of the quality of aerosol produced by an EHD device. In one embodiment of the present invention an ionic compound (e.g., salt) such as sodium chloride, sodium acetate, benzalkonium chloride, or lecithin, is added to further adjust electrical resistivity, thereby facilitating control of aerosol particle size.

In another embodiment of the present invention, surfactants such as lecithin, polysorbates, poloaxamers, sorbitan esters, glycerides, ethoxylated alcohols, ethoxylated phenols, and ethylene oxide-propylene oxide copolymers are added to lower the surface tension of the liquid. In a preferred embodiment, non-ionic ethoxlyated decyl alcohol (Desonic DA-4) having hydrophilic-lipophilic balance (HLB) of about 10.5 is added to highly aqueous compositions to enhance the dispersion characteristics of the composition. The present invention contemplates the use of both pulmonary surfactant and other natural or synthetic surfactants.

In another embodiment of the present invention, suspending agents such as celluloses, polyvinyl pyrrolidone (povidone or PVP), polyvinyl alcohol (PVA), triglycerides, ethoxylated oils, polyethyl glycol, saccharide gums, and alginates may be added to facilitate suspension of particles, or creation of an emulsion, in a liquid composition.

In still another embodiment of the present invention, adjuvants such as clove oil, citric acid, caffeine, vaccine adjuvants such as alum, polymers, macromolecules, and oligonucleotides are added to provide enhanced synergistic efficacy effect between the active ingredient and the excipient.

Excipients may also be added to enhance or increase the patient's ability to receive the aerosolized composition. For example, in one embodiment of the present invention, sugars, including sucrose, trehalose, and mannitol, are added either to stabilize compositions containing proteins, or to serve as sweeteners to improve the taste of the composition. In other embodiments, flavoring agents such as sugars, oils, citric acid, menthol, and camphor are added to improve the flavor of a composition.

EXAMPLES

The following examples of possible liquid compositions for aerosolization with an electrohydrodynamic device are meant to be illustrative of the invention, and are not meant to limit the full breadth of the invention disclosed herein.

Aerosol Composition 1

Paclitaxel (drug) 75 mg/ml paclitaxel in 80% ethanol; 19.8% polyethylene glycol; 0.2% citric acid.

Aerosol Composition 2

Sodium Cromoglycate (drug) 1% solution of sodium cromoglycate; 50% ethanol; 49% propylene glycol.

Aerosol Composition 3

Albuterol Sulfate (drug) 0.25% solution of albuterol sulfate; 70% ethanol; 29.75% water.

Aerosol Composition 4

Triamcinolone Acetonide (drug) 1% solution of triamcinolone acetonide; 70% ethanol; 29% glycerol.

While the above description discloses specific composition ingredients, ranges, and: other specificities, these should not be construed as limitations on the scope of the invention, but rather as exemplification of typical embodiments thereof. Numerous other variations are possible, and it is not intended herein to mention all of the possible equivalent forms or ramifications of the invention. Various changes may be made to the present invention without departing from the scope of the invention.

What is claimed is:

1. A method for delivering a biologically active material to the respiratory tract of a patient in need of treatment comprising the steps of:
   a) producing an aerosol of a liquid composition using an electrohydrodynamic spraying/aerosolization means; and
   b) administering said aerosol to the pulmonary tract of said patient via inhalation of said aerosol;
   wherein said liquid composition comprises a pharmaceutically effective amount of a biologically active material and a carrier liquid in which said active material is dissolved, emulsified, or suspended; and wherein said liquid composition has the following properties:
      (i) a surface tension of from about 10 to about 72 milliNewtons/meter;
      (ii) an electrical resistivity of from about 10 to about 100,000 ohm-meters; and
      (iii) an electrical permittivity of from about 5 to about 500; and
   wherein said aerosol has a particle size of from about 0.1 to from about 10 μm in diameter.

2. The method according to claim 1, wherein said surface tension is from about 15 to from about 45 milliNewtons/meter, wherein said electrical resistivity is from about 50 to from about 10,000 ohm-meters, and wherein said electrical permittivity is from about 10 to 500.

3. The method according to claim 2 wherein said surface tension is from about 20 to from about 35 milliNewtons/meter, wherein said electrical resistivity is from about 200 to from about 2000 ohm-meters, and wherein said electrical permittivity is from about 15 to from about 50.

4. The method according to claim 1 wherein said carrier material is selected from the group consisting of water, an alcohol, and a perfluorocarbon or mixtures thereof.

5. The method according to claim 4 wherein said carrier material is a mixture of ethanol and water.

6. The method according to claim 4 wherein said alcohol is selected from the group consisting of ethanol or isopropanol.

7. The method according to claim 6 wherein said alcohol is ethanol.

8. The method according to claim 1 wherein said carrier liquid consists essentially of a carrier material, an aerosol properties adjusting material and a pharmaceutically acceptable excipient, wherein said aerosol properties adjusting material is selected from the group consisting of propylene glycol, polyethylene glycol, glycerol, oleic acid, medium chain triglycerides, fatty acids, soybean oil, and olive oil.

9. The method according to claim 8, wherein said surface tension is from about 15 to from about 45 milliNewtons/meter, wherein said electrical resistivity is from about 50 to from about 10,000 ohm-meters, and wherein said electrical permittivity is from about 10 to 500.

10. The method according to claim 9 wherein said surface tension is from about 20 to from about 35 milliNewtons/meter, wherein said electrical resistivity is from about 200 to from about 2000 ohm-meters, and wherein said electrical permittivity is from about 15 to from about 50.

11. The method according to claim 8 wherein said pharmaceutically acceptable excipient is selected from the group consisting of antioxidants, ionic agents, surfactants, preservatives, suspending agents, sweeteners, and flavoring agents.

12. The method according to claim 8 wherein said active material is selected from the group consisting of a drug, a vaccine, a nucleic acid, an aptamer, a gene therapy agent, an enzyme, a hormone, an antibody, a vitamin, a protein, a peptide, a polypeptide, an oligonucleotide, a cell, an antigen, an allergen, a natural surfactant, and a synthetic surfactant.

13. The method according to claim 12 wherein said active material is selected from the group consisting of sodium cromoglycate, albuterol sulfate, triamcinalone, doxorubicin, and paclitaxel.

14. The method according to claim 12 wherein said active ingredient is selected from the group consisting of a protein, a peptide and a polypeptide.

15. The method according to claim 8 wherein said carrier material is selected from the group consisting of water, an alcohol, and a perfluorocarbon or mixtures thereof.

16. The method according to claim 15 wherein said aerosol properties adjusting material is selected from the group consisting of propylene glycol, polyethylene glycol, glycerol, oleic acid, medium chain triglycerides, fatty acids, soybean oil, and olive oil.

17. The method according to claim 16 wherein said aerosol properties adjusting material is selected from the group consisting of propylene glycol, polyethylene glycol and glycerol.

18. The method according to claim 17 wherein said carrier material is ethanol.

* * * * *